US00PP37757P2

(12) United States Plant Patent
Hansen et al.

(10) Patent No.: US PP37,757 P2
(45) Date of Patent: Oct. 13, 2026

(54) ***AJUGA* PLANT NAMED 'Rosy Robin'**

(50) Latin Name: *Ajuga reptans*
Varietal Denomination: Rosy Robin

(71) Applicants: Christopher M. Hansen, Zeeland, MI (US); Curtis J. Andersen, Spring Lake, MI (US); Jacob T. Schimmel, Hudsonville, MI (US)

(72) Inventors: Christopher M. Hansen, Zeeland, MI (US); Curtis J. Andersen, Spring Lake, MI (US); Jacob T. Schimmel, Hudsonville, MI (US)

(73) Assignee: GARDEN SOLUTIONS, LLC, Zeeland, MI (US)

( * ) Notice: Subject to any disclaimer, the term of this patent is extended or adjusted under 35 U.S.C. 154(b) by 0 days.

(21) Appl. No.: 19/372,580

(22) Filed: Oct. 29, 2025

(51) Int. Cl.
*A01H 6/00* (2018.01)
*A01H 5/02* (2018.01)

(52) U.S. Cl.
USPC ..... Plt./401

(58) Field of Classification Search
USPC ..... Plt./401
CPC ..... A01H 6/00; A01H 6/50; A01H 5/02
See application file for complete search history.

(56) References Cited

PUBLICATIONS

Feathered Friends (gardensolutionsplants.com/feathered-friends) (Year: 2021).*

* cited by examiner

*Primary Examiner* — Keith O. Robinson
(74) *Attorney, Agent, or Firm* — Penny J. Aguirre

(57) ABSTRACT

A new cultivar of *Ajuga* plant named 'Rosy Robin' that is characterized by its bright orange new foliage that is present for 9 months of the year, its leaves that are small in size, its vigorous growth habit, and its light pink flowers.

2 Drawing Sheets

Botanical classification: *Ajuga reptans.*
Variety denomination: 'Rosy Robin'.

BACKGROUND OF THE INVENTION

The present invention relates to a new and distinct cultivar of *Ajuga reptans* and will be referred to hereafter by its cultivar name, 'Rosy Robin'. 'Rosy Robin' represents a new cultivar of *Ajuga*, an herbaceous perennial grown for landscape use.

The new Invention arose from an ongoing controlled breeding program in Hudsonville, Michigan. The goal of the breeding program is to develop a new cultivar of *Ajuga* with orange foliage coloration, pink flowers, small leaf size, vigorous growth habit, and a floriferous, freely blooming habit. The new cultivar arose from a controlled cross made in February of 2022 between *Ajuga* 'TROTOU' (U.S. Plant Pat. No. 34,616) as the female parent and *Ajuga* 'FANFIN' (U.S. Plant Pat. No. 34,650) as the male parent. The Inventors selected 'Rosy Robin' as a single unique plant from amongst the seedlings of the above cross in April of 2024.

Asexual propagation of the new cultivar was first accomplished by stem tip cuttings under the direction of the Inventors in Hudsonville, Michigan in March of 2023. Asexual propagation by tip stem cuttings has determined that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'Rosy Robin' as a unique cultivar of *Ajuga.*

1. 'Rosy Robin' exhibits bright orange new foliage that is present for 9 months of the year.
2. 'Rosy Robin' exhibits leaves that are small in size.
3. 'Rosy Robin' exhibits a very floriferous blooming habit.
4. 'Rosy Robin' exhibits a vigorous growth habit.
5. 'Rosy Robin' exhibits light pink flowers.

The female parent plant of 'Rosy Robin' differs from 'Rosy Robin' in having leaves that are larger in size and yellow in color, flowers that are blue in color, and much fewer flowering stems. The male parent plant of 'Rosy Robin' differs from 'Rosy Robin' in having flowers that are blue in color. 'Rosy Robin' can be most closely compared to *Ajuga reptans* cultivars 'CORCAN' (U.S. Plant Pat. No. 34,673) and 'Fancy Finch' (U.S. Plant Pat. No. 34,650). 'Cordial Canary' is similar to 'Rosy Robin' in having small leaves. 'Cordial Canary' differs from 'Rosy Robin' in having flowers that are blue in color, fewer flowering stems, and yellow leaves.

STATEMENT REGARDING PRIOR DISCLOSURES BY THE INVENTORS

The Applicants assert that no publications or advertisements relating to sales, offers for sale, or public distribution occurred more than one year prior to the effective filing date of this application. Any information about the claimed plant would have been obtained from a direct or indirect disclosure from the Inventors. The Applicants claim a prior art exemption under 35 U.S.C. 102(b)(1) for disclosure and/or sales prior to the filing date but less than one year prior to the effective filing date. Disclosures include but are not limited to a website publication by Garden Solutions Plants.

BRIEF DESCRIPTION OF THE DRAWINGS

The accompanying color photographs illustrate the overall appearance and distinct characteristics of the new *Ajuga* as grown in a 1-gallon pot, 8-months in age in Hudsonville, Michigan.

The photograph in FIG. 1 provides a side view of a plant 'Rosy Robin' in bloom.

Figure 1:
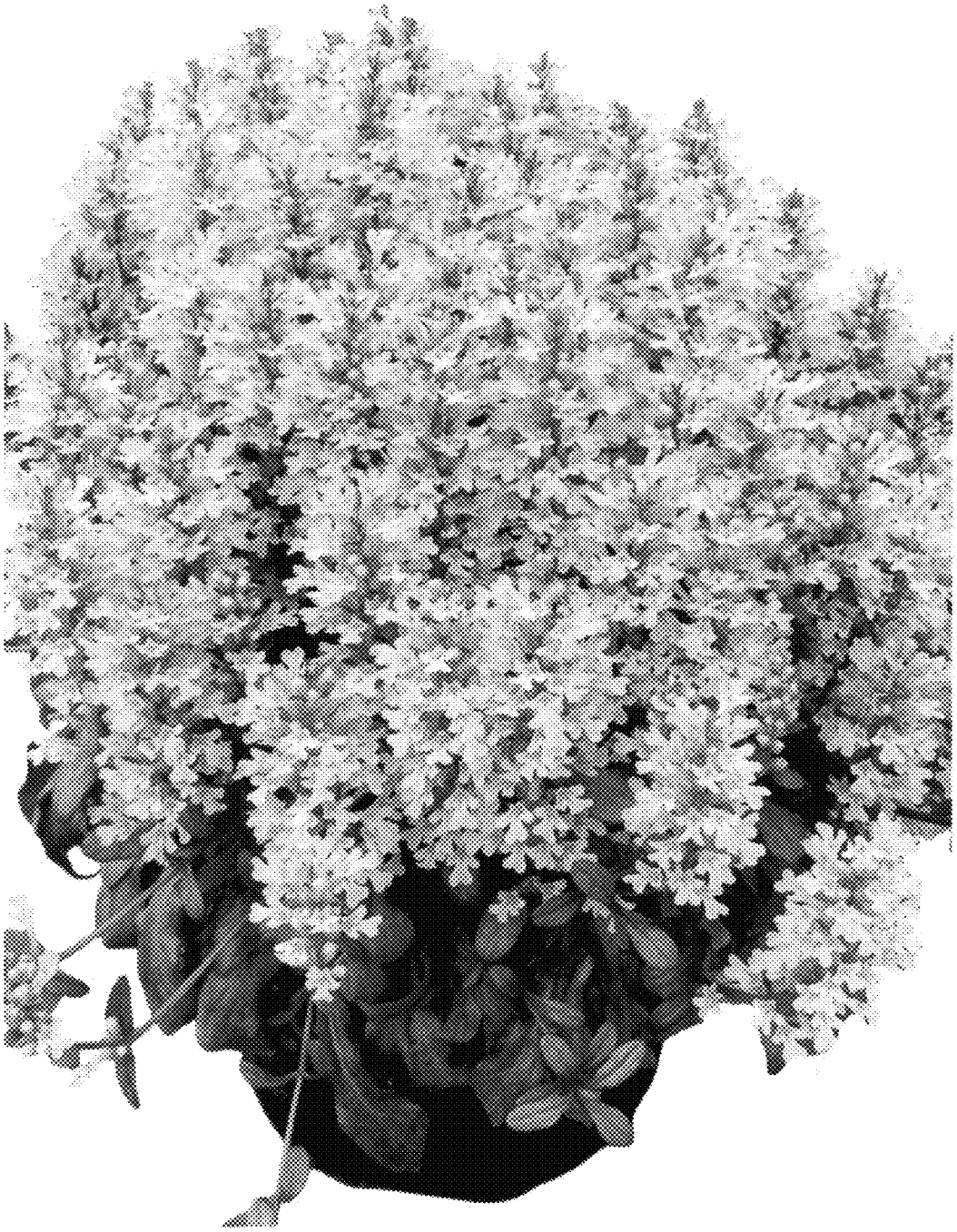
Figure 2:
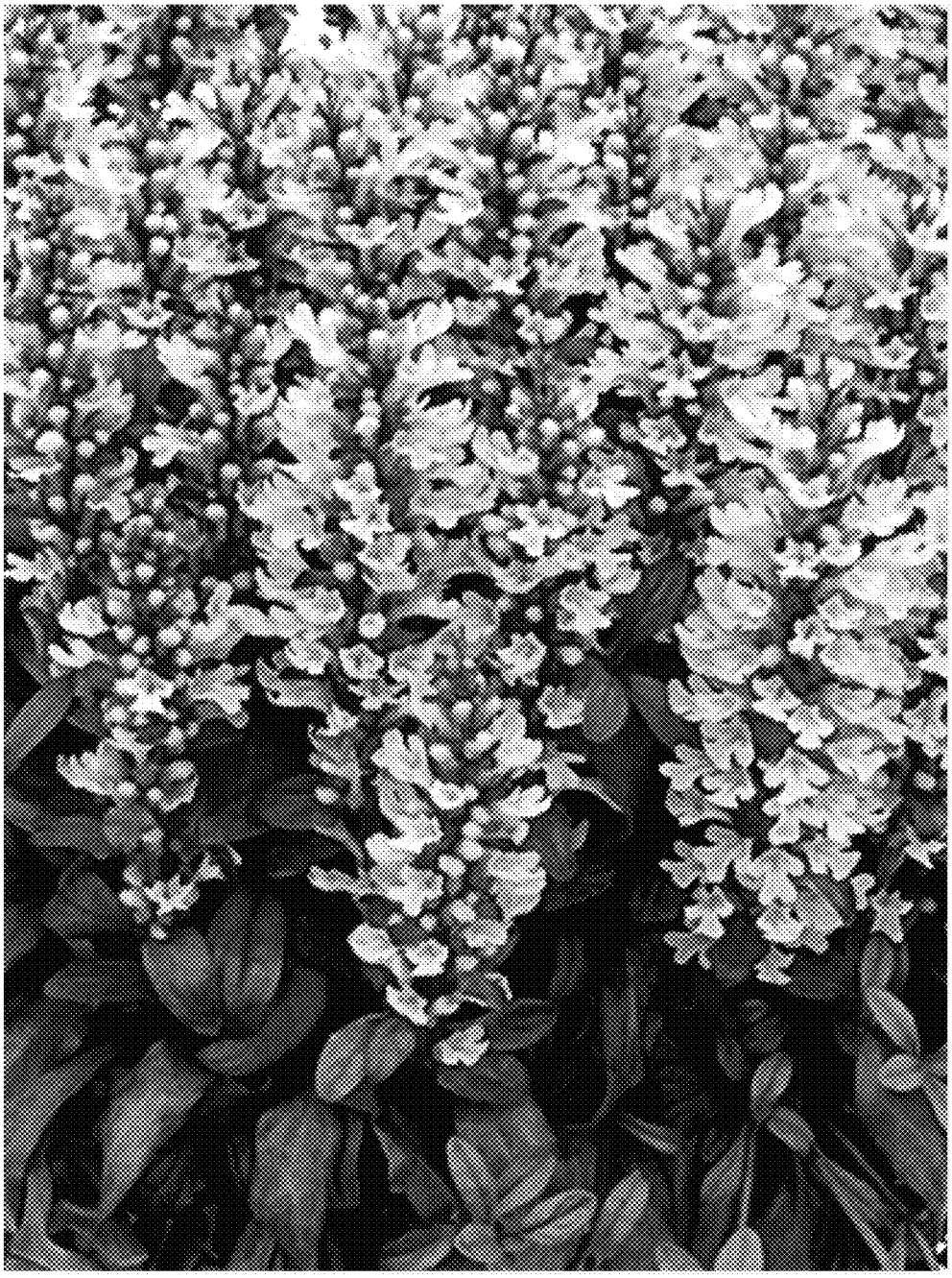

The photograph in FIG. 2 provides a close-up view of the inflorescences of 'Rosy Robin'.

The colors in the photograph may differ slightly from the color values cited in the detailed botanical description, which accurately describe the colors of the new *Ajuga.*

DETAILED BOTANICAL DESCRIPTION

The following is a detailed description of the new cultivar as observed on 10-month-old plants of the new *Ajuga* as grown in 1-gallon containers in a greenhouse in Hudsonville, Michigan. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—5.5 weeks in mid spring in Michigan.

*Plant type*.—Herbaceous perennial.

*Plant habit*.—Dense and rounded, compact upright inflorescences.

*Height and spread.*—25 cm in height (soil level to top of floral plane), an average of 18 cm in height (soil level to top of foliar plane), 20 cm in width (includes runners) as a eight-month-old plant as grown in a container, reaches about 45 cm in width as a 2-year-old plant in the landscape.

*Cold hardiness*.—At least in U.S.D.A. Zones 4 to 9.

*Diseases and pests*.—Highly resistance to powdery mildew (caused by *Golovinomyces biocellatus* and *Neoerysiphe galeopsidis*).

*Root description*.—Fine and fibrous, a blend of 158A and NN155A in color.

*Propagation type*.—Stem tip cuttings.

*Root development*.—Time required for root initiation; 10 days, time required to produce a young plant from a rooted cutting; 6 weeks to produce a 72-cell plug.

*Growth rate*.—Very vigorous.

*Branching habit*.—Basal rosettes of leaves from rhizomes, produces stolons.

Branch description (runners):

*Stolons*.—Quickly spreading growing horizontal to the ground, produces an average of 15 per plant, 25 cm in length, 2 mm in diameter, color; 158A and 148A, flushed with and then eventually changing to 182A and 182B, surface is glossy and sparsely covered with soft hairs 0.5 mm in length and NN155D in color.

Foliage description:

*Leaf shape*.—Spatulate.

*Leaf division*.—Simple.

*Leaf base*.—Truncate.

*Leaf apex*.—Rounded.

*Leaf venation*.—Pinnate, veins are moderately sunken in the leaves, colors match leaf colors.

*Leaf margins*.—Moderately undulate.

*Leaf attachment and arrangement*.—Whorled, held in clumps.

*Leaf orientation*.—Various angles, mostly horizontal.

*Leaf surface*.—Rugose, very finely puberulent and slightly rough to the touch on upper and lower surface.

*Leaf color*.—Young upper and lower surface; a blend of 150B, 152A, 183A, and N170A, flushed with 182A at the base and around the margins, mature upper and lower surface; a blend of 144A, NN137A, and 145A.

*Leaf size*.—Up to 4 cm in length and 2 cm in width.

*Leaf quantity*.—Very dense, an average of 70 leaves per plant inside the dense clump, runners have an average of 20 per runner.

*Leaf attachment*.—Sessile.

Flower description:

*Inflorescence type*.—Verticillaster, terminal spike, individual flowers in clusters held in leaf-axils.

*Inflorescence size*.—An average of 7 cm in height and 3 cm in width.

*Inflorescence number*.—Average of 20.

*Lastingness of inflorescence.*—10 to 14 days, self-cleaning.

*Flower type*.—Labiate.

*Flower number*.—Average of 80 per inflorescence.

*Flower fragrance*.—None.

*Flower buds*.—Oblanceolate in shape, average of 6 mm in length and 2.5 mm in diameter, color; 182B, immature calyx 157B, surface matte and densely covered with soft woolly pubescence.

*Flower size*.—Average of 1 cm in depth, 5 mm in diameter, throat diameter 1.5 mm, tube 6 mm in length and 1.5 mm in diameter.

*Peduncles*.—An average of 3 cm in length, 5 mm in diameter, vertical angle, moderately strong, color; 148A, flushed with 182A and 182B, surface is glossy and sparsely covered with very short hairs that match surface color.

*Calyx*.—Rotate and tubular in shape, 2 mm in length and diameter.

*Sepals.*—5, 50% fused at base, average of 1.5 mm in length, 1 mm in width, ovate in shape, apex acute, entire margins, surface is covered with long woolly hairs matching surface color, color inner and outer surface 145A and 144A, becoming flushed with 178A.

*Petals.*—40% of petals fused into tube, central lobe; notched and fused, average of 7 mm in length, 6 mm in width, outer lobes; average of 5 mm in length, 4 mm in width, all lobes; blunt and rounded in shape, obtuse apex, entire margins that are slightly undulated, both surfaces are glabrous, matte and papery texture, color: upper and lower surface when opening; NN155D, upper and lower surface when fully open; NN155D, randomly flushed with 69C, flower throat; outer surface covered with woolly soft pubescence, inner surface is smooth and glabrous, color; inner and outer surface when opening and fully open NN155D, flower tube; both surfaces glabrous, color inner and outer surface when opening and fully open NN155D, base flushed with 65B.

Reproductive organs:

*Pistils.*—1, style; 7 mm in length, NN155D in color, stigma; non-distinguishable, ovary; oblong, 1.5 mm in length, 1 mm in width, NN155D in color.

*Stamens.*—5, filament; implanted into flower tube, average of 6 mm in length, NN155D in color, anthers; club-shaped, 0.8 mm in diameter, 203A in color, pollen; moderate, 10D.

*Fruit and seed.*—Fruit and seed production has not been observed to date.

It is claimed:

1. A new and distinct variety of *Ajuga* plant named 'Rosy Robin' as described and illustrated herein.

* * * * *